United States Patent [19]

Sobotta et al.

[11] Patent Number: 5,006,533

[45] Date of Patent: Apr. 9, 1991

[54] CERTAIN 3-BROMO-2,6-DIMETHOXYBENZAMIDES AND PHARMACEUTICAL USE THEREOF

[75] Inventors: Rainer Sobotta, Ingelheim am Rhein; Adolf Langbein, Gau-Algesheim; Herbert Merz, Ingelheim am Rhein; Rudolf Bauer, Wiesbaden; Joachim Mierau, Mainz, all of Fed. Rep. of Germany

[73] Assignee: Boehringer Ingelheim GmbH, Ingelheim am Rhein, Fed. Rep. of Germany

[21] Appl. No.: 440,917

[22] Filed: Nov. 22, 1989

Related U.S. Application Data

[63] Continuation of Ser. No. 294,852, Jan. 9, 1989, abandoned, which is a continuation of Ser. No. 90,866, Aug. 28, 1987, abandoned.

[30] Foreign Application Priority Data

Aug. 30, 1986 [DE] Fed. Rep. of Germany ....... 3629598

[51] Int. Cl.$^5$ .................... A61K 31/46; C07D 451/04
[52] U.S. Cl. .................................... 514/304; 546/131
[58] Field of Search ......................... 546/131; 514/304

[56] References Cited

U.S. PATENT DOCUMENTS

| 4,321,378 | 3/1982 | Dostert et al. | 546/124 |
| 4,336,259 | 6/1982 | Hadley et al. | 546/124 |

FOREIGN PATENT DOCUMENTS

| 0004831 | 10/1979 | European Pat. Off. | |
| 0095262 | 11/1983 | European Pat. Off. | 546/131 |
| 3340629 | 5/1985 | Fed. Rep. of Germany. | |

*Primary Examiner*—Bernard I. Dentz
*Attorney, Agent, or Firm*—David E. Frankhouser; Mary-Ellen M. Timbers

[57] ABSTRACT

3-Bromo-2,6-dimethoxybenzamides useful as neuroleptic agents are described.

5 Claims, No Drawings

CERTAIN 3-BROMO-2,6-DIMETHOXYBENZAMIDES AND PHARMACEUTICAL USE THEREOF

This is a continuation of application Ser. No. 294,852, filed Jan. 9, 1989, which is a continuation of Ser. No. 090,866 filed Aug. 28, 1987 both now abandoned.

The invention relates to new 3-bromo-2,6-dimethoxybenzamides, the preparation thereof and their use as pharmaceutical compositions.

The new compounds correspond to formula

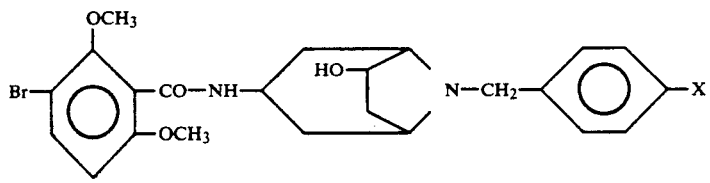
(I)

wherein X represents hydrogen, fluorine or chlorine; they may occur as free bases or as acid addition salts.

Formula I includes both mixtures of enantiomers and also pure enantiomers.

In order to prepare these compounds a corresponding 3-amino-6-hydroxy-nortropane of formula

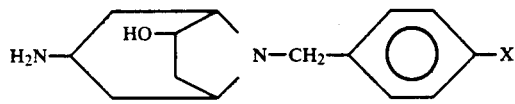
(II)

wherein X is defined as hereinbefore, may be reacted with a benzoic acid derivative of formula

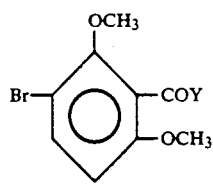
(III)

wherein Y represents a group which can be split off as HY with a hydrogen atom of the amino group in II.

If during working up the reaction product I is obtained as a free base, it may subsequently be converted in the usual way into a desired acid addition salt, preferably a salt of addition with a physiologically acceptable acid. Mixtures of enantiomers obtained may be resolved by conventional methods. It is also possible to use compounds of formula II in the form of the pure enantiomers. Examples of the group Y include OH, chlorine, bromine, CNCH2O—, ethoxycarbonyloxy and imidazolyl.

If dimethoxybenzoyl halides of formula III are used, the calculated quantity of the acylating agent or an excess thereof is used and the work is appropriately done in the presence of an acid binding substance such as dicyclohexylethylamine, sodium carbonate, potassium carbonate, calcium oxide or preferably triethylamine. Although the use of solvents is not essential, it is advantageous to carry out the reaction in an inert solvent such as chloroform, toluene, nitromethane, tetrahydrofuran, dimethyl formamide or preferably methylene chloride. The reaction temperature is variable within wide limits. Temperatures of around 20° C. or below are convenient.

Acylation of the compounds of formula II by means of a carboxylic acid imidazolide is effected by reacting the corresponding 2,6-dimethoxybenzoic acid first with carbonyldiimidazole and subsequently with the amine. The calculated quantity of carboxylic acid and equivalent quantities of carbonyldiimidazole are used. The reaction is carried out in inert solvents. Tetrahydrofuran has proved particularly favourable. The reaction temperature is variable within limits. The reaction is best performed at between 0° and 10° C.

The reaction products obtained by this method are isolated from the reaction mixtures by known methods. If desired, the crude products obtained may also be purified using special procedures, e.g. column chromatography, before being crystallized in the form of bases or suitable acid addition compounds.

The 2,6-dimethoxybenzamides of formula I according to the invention may be converted in the usual way into their physiologically acceptable acid addition salts. Acids suitable for salt formation include, for example, hydrochloric, hydrobromic, hydriodic, hydrofluoric, sulphuric, phosphoric, nitric, acetic, propionic, butyric, caproic, valeric, oxalic, malonic, succinic, maleic, fumaric, lactic, tartaric, citric, malic, benzoic, p-hydroxybenzoic, p-aminobenzoic, phthalic, cinnamic, salicylic, ascorbic and methanesulphonic acid and 8-chlorotheophyllin.

The starting materials of formulae II and III are known or may be obtained by conventional methods.

Starting compounds of formula II may be obtained by the following synthesis plan (where X=F, Cl):

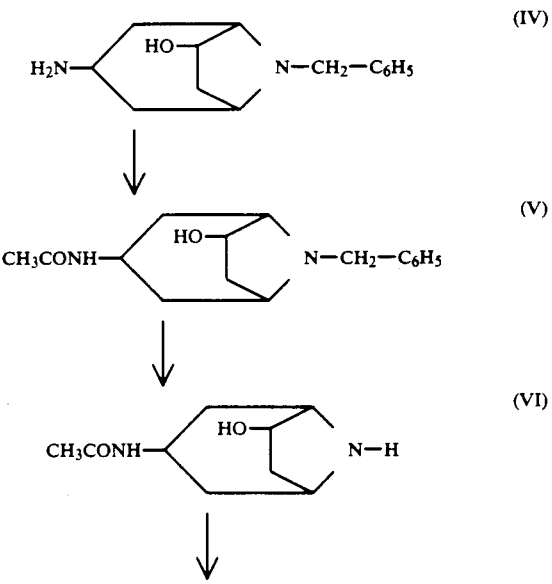

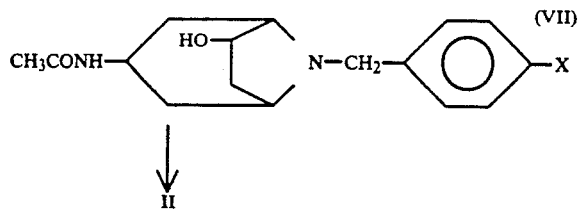

Compound IV is known from published European patent application No. 0,004,831.

The new compounds of formula I show the typical pattern of activity of neuroleptic agents and can therefore be used as CNS-suppressant agents. Compared with known compounds of similar structure, particular mention should be made of the favourable differentiation between antidopaminergic primary effects and dyskinetic side effects.

The new compounds were subjected to pharmacological investigation in numerous tests.

In the apomorphine climbing test on the mouse (B. Costall et al., Europ. J. Pharmacol. 50, 39 ff (1978), modified) they demonstrate powerful apomorphine-antagonistic activities which in some cases substantially exceed those of the comparison compounds mentioned above. These properties would lead one to expect neuroleptic effects in humans, on the basis of the prior art. Owing to the close structural affinity with the compounds known from European Patent No. 4 831 these properties were surprising and unforeseeable. The following test arrangements were used to determine any side effects such as sedation or disruption of motor coordination: The Measurement of Motility in Mice according to T. H. SVENSSON and G. THIEME, Pyschopharmacol. (Berlin) 14, 157 ff (1969), modified, gives some indication of sedative effects. The ataxia test using a rotating rod (Rotarod) in mice according to N. W. DUNHAM and T. S. MIYA, J. Amer. Pharm. Assoc. Sci. Ed. 46, 208 ff (1957), modified, provides indications of disruptions to motor coordination.

The dyskinetic effects are among the most disturbing side effects of neuroleptic drugs. These include Parkinsonian manifestations such as tremor, rigidity and akinesia but also dyskinesia in the mouth-tongue-pharynx region.

The investigation of such symptoms in an animal model is possible using rhesus monkeys sensitised with haloperidol. After being given neuroleptic drugs, which have extrapyramidal motor effects in humans, these animals show typical dyskinesia in the mouth and tongue region (according to J. Liebmann and R. Neale, Psychopharmacology 68, 25-29 (1980) modified).

With regard to side effects, the compounds for which protection is claimed behave more favourably than the comparison substances.

The superiority of the compounds according to the invention over the structurally most similar compound from the prior art, namely N-(8-benzyl-3-nortropanyl)-2,6-dimethoxy-3-bromobenzamide (Compound A; cf. DE-A No. 3 340 629, Example 2), is clear from the pharmacological data in the following Table:

| Compound | Climbing test $ED_{50}$ [mg/kg] after 1 h | Dyskinesia threshold dose p.o. [mg/kg] | Dyskinesia index I:II | $LD_{50}$ (mouse) p.o. [mg/kg] |
|---|---|---|---|---|
| A (known) | 1.8 | 10 | 0.18 | ~300 |
| according to the invention: Formula I, | | | | |
| X = H | 1.2 | >15 | <0.08 | ~300 |
| X = F | 0.63 | 8 | 0.078 | >300<600 |
| X = Cl | 0.85 | 30 | 0.028 | >1000 |

The compounds according to the invention may be used on their own or combined with other active substances. Suitable forms for administration include tablets, capsules, suppositories, solutions, syrups, emulsions and dispersible powders. Tablets may be produced, for example, by mixing the active substance or substances with known excipients, e.g. inert diluents such as calcium carbonate, calcium phosphate or lactose, disintegrants such as corn starch, alginic acid, binders such as starch or gelatine, lubricants such as magnesium stearate or talc and/or agents for obtaining delayed release such as carboxypolymethylene, carboxymethylcellulose, cellulose acetate phthalate or polyvinylacetate.

The new compounds may be administered by enteral or parenteral route. For oral administration, single doses of 0.5 to 10 mg, preferably 1 to 5 mg may be used.

EXAMPLES OF PHARMACEUTICAL FORMULATIONS

| (a) Coated tablets | |
|---|---|
| 1 tablet core contains: | |
| Active substance of formula I | 2.0 mg |
| Lactose | 28.5 mg |
| Corn starch | 17.0 mg |
| Gelatine | 2.0 mg |
| Magnesium stearate | 0.5 mg |
| | 50.0 mg |

Method

The active substance is mixed with lactose and corn starch and the mixture is granulated with a 10% aqueous gelatine solution by passing through a screen with a 1 mm mesh, then dried at 40° C. and passed through another screen. The granulate thus obtained is mixed with magnesium stearate and compressed. The cores thus obtained are coated in the usual way with a coating formed from an aqueous suspension of sugar, titanium dioxide, talc and gum arabic. The finished coated tablets are polished with beeswax. Final weight of coated tablet: 100 mg

| (b) Tablets | |
|---|---|
| Active substance of formula I | 2.0 mg |
| Lactose | 55.0 mg |
| Corn starch | 38.0 mg |
| Soluble starch | 4.0 mg |
| Magnesium stearate | 1.0 mg |
| | 100.0 mg |

Method

The active substance and magnesium stearate are granulated with an aqueous solution of the soluble starch, the granulate is dried and intimately mixed with lactose and corn starch. The mixture is then compressed to form tablets weighing 100 mg, containing 2 mg of active substance.

| (c) Suppositories | |
| --- | --- |
| 1 suppository contains: | |
| Active substance of formula I | 1.0 mg |
| Suppository mass | 1699.0 mg |

Method

The finely powdered substance is stirred, using an immersion homogeniser, into the molten suppository mass which has been cooled to 40° C. At 35° C. the mass is poured into slightly chilled moulds.

| (d) Ampoules | |
| --- | --- |
| Active substance of formula I | 2.0 mg |
| Sodium chloride | 18.0 mg |
| Distilled water, add | 2.0 ml |

Method

The active substance and sodium chloride are dissolved in water, the solution is filtered to remove any suspended particles and transferred into 2 cc ampoules under aseptic conditions. Finally the ampoules are sterilised and sealed. Each ampoule contains 2 mg of active substance.

The Examples which follow are intended to illustrate the invention.

PREPARATION OF STARTING MATERIALS

(a) 3-Acetamido-6-hydroxy-8-benzylnortropane 10.1 g of acetyl chloride (0.129 mol) are added dropwise at 20° C. to a solution of 30 g of 3-amino-6-hydroxy-8-benzylnortropane (0.129 mol) and 13.1 g of triethylamine (0.129 mol) in 250 ml of methylene chloride. The mixture is then refluxed for 3 hours. After cooling, the solution is washed once with 200 ml of 10% sodium hydroxide solution and three times with 200 ml of water. After the methylene chloride phase has been dried over sodium sulphate, 28.4 g of white crystals (80.2% of theory) are obtained, m.p. 108° C., by distilling off the solvent.

(b) 3-Acetamido-6-hydroxynortropane 28.4 g of 3-Acetamido-6-hydroxy-8-benzylnortropane (0.104 mol) dissolved in 300 ml methanol, are hydrogenated in a shaking autoclave, after the addition of 2.8 g of 5% palladium on charcoal, at 20° C. under a hydrogen pressure of 5 bar. After the uptake of hydrogen has ceased the solution is separated from the catalyst by filtration and evaporated down in vacuo. The initially oily residue is crystallized from a mixture of ethyl acetate and ethanol 9:1. 16.2 g of white crystals are obtained (85% of theory) with a m.p. of 173° C.

(c) Acetamido-6-hydroxy-8-(4-chlorobenzyl)-nortropane 5.04 g of sodium bicarbonate (0.06 mol) are added to a solution of 5.53 g of 3-acetamido-6-hydroxynortropane (0.03 mol) in 50 ml of a solvent mixture (dimethylformamide/tetrahydrofuran; 4:1). After 5.31 g of 4-chlorobenzyl chloride (0.033 mol) dissolved in 10 ml of solvent mixture have been added dropwise the mixture is refluxed for 7 hours. After cooling, the solvent mixture is distilled off in vacuo. The residue is combined with 200 ml of water and extracted three times, each time with 100 ml of methylene chloride. The combined methylene chloride phases are dried over sodium sulphate and evaporated down in vacuo. 8.9 g of white crystals are obtained, 96% of theory, m.p. 105° C.

(d) Acetamido-6-hydroxy-8-(4-fluorobenzyl)-nortropane

This compound is prepared and worked up as in the preparation of 3-acetamido-6-hydroxy-8-(4-chlorobenzyl)-nortropane. From 5.53 g of 3-acetamido-6-hydroxy-nortropane (0.023 mol), 6.08 g of 4-fluorobenzylbromide (0.033 mol), 5.7 g of white crystals are obtained (65% of theory), m.p. 125° C.

(e) 3-Amino-6-hydroxy-8-(4-fluorobenzyl)-nortropane 8.9 g of 3-acetamido-6-hydroxy-8-(4-fluorobenzyl)-nortropane are refluxed for 7 hours in 100 ml of 6N hydrochloric acid. After cooling, the mixture is concentrated to dryness in vacuo. The residue is dissolved in alcohol and brought to crystallization by the addition of ethyl acetate to give a ratio of 1:1. 4.74 g of white crystals of the dihydrochloride are obtained, m.p. 250° C.; yield 77.7% of theory.

1.6 g of sodium methoxide (29.6 mmol) are added to 4.74 g of dihydrochloride (14.8 mmol) dissolved in methanol, and the mixture is stirred for 10 minutes. The suspension produced is filtered over kieselguhr and the filtrate is concentrated to dryness in vacuo. 3.7 g of white crystals of the base are obtained, m.p. 130° C.

(f) 3-Amino-6-hydroxy-8-(4-chlorobenzyl)-nortropane

The title compound is prepared and worked up in the same way as 3-amino-6-hydroxy-8-(4-fluorobenzyl)-nortropane. From 8.9 g of 3-acetamido-6-hydroxy-8-(4-chlorobenzyl)-nortropane, 5.38 g of white crystals are obtained, 47.7% of theory of the dihydrochloride, m.p. 300° C. Liberation of the base yields 4.6 g of beige crystals, m.p. 145° C.

PREPARATION OF THE END PRODUCTS

Example 1

N-(8-Benzyl-6-hydroxy-3-nortropanyl)-2,6-dimethoxy-3-bromobenzamide fumarate

One drop of dimethylformamide is added to 5.22 g of 2,6-dimethoxy-5-bromobenzoic acid (20 mmol) dissolved in 60 ml of methylene chloride, then 3.5 ml of oxalic chloride are slowly added dropwise at 20° C. When the reaction mixture is releasing only a little gas, it is boiled for a further 20 minutes. The solvent is distilled off. The residue is dissolved in 40 ml of dry methylene chloride and added dropwise at ambient temperature to a solution of 4.64 g of 3-amino-6-hydroxy-8-benzyl-nortropane (20 mmol) and 7.2 ml of triethylamine in 60 ml of methylene chloride. The mixture is left to react for 3 hours and then worked up. The solution is diluted with 100 ml of methylene chloride, then washed twice with 100 ml of water and then with 10% sodium hydroxide solution.

The organic phase is dried over sodium sulphate and concentrated by evaporation. The residue is dissolved in methanol and the salt is crystallized out by the addition of 2.32 g of fumaric acid (in methanol). 8.6 g of white crystals (72.7% of theory) are obtained, m.p. 144° C.

| Elementary analysis: | | | |
|---|---|---|---|
| $C_{23}H_{27}BrN_2O_4$ Calculated | C 54.83 | H 5.28 | N 4.74 |
| 591.47 Found | C 54.92 | H 5.38 | N 4.70 |

Example 2

N-[8-(4-Fluorobenzyl)-6-hydroxy-3-nortropanyl]-2,6-dimethoxy-3-bromobenzamide-hydrochloride The compound is prepared and worked up as in Example 1. From 1.93 g of 2,6-dimethoxy-5-bromobenzoic acid, 0.94 g of oxalyl chloride, 0.75 g of triethylamine and 1.85 g of 3-amino-6-hydroxy-8-(4-fluorobenzyl)-nortropane the crude base is obtained, which yields, with methanolic hydrochloric acid, 1.8 g of white crystals, m.p. 140° C. in a yield of 44% of theory.

| Elementary Analysis: | | | |
|---|---|---|---|
| $C_{23}H_{26}BrFN_2O_4 \times HCl$ Calculated | C 52.14 | H 5.14 | N 5.29 |
| 529.84 Found | C 51.53 | H 5.53 | N 4.94 |

Example 3

N-[8-(4-Chlorobenzyl)-6-hydroxy-3-nortropanyl]-2,6-dimethoxy-3-bromobenzamide-hydrochloride Prepared and worked up as in Example 1. From 11.55 g of 2,6-dimethoxy-5-bromobenzoic acid, 5.63 g of oxalic chloride, 4.49 g of 3-amino-6-hydroxy-8-(4-chlorobenzyl)-nortropane in 200 ml of methanol, 17 g (75% of theory) of white crystals of the base are obtained, m.p. 179° C. Using methanolic hydrochloric acid, white crystals of the hydrochloride are formed, m.p. 162°–165° C.

| Elementary analysis: | | | |
|---|---|---|---|
| $C_{23}H_{26}BrClN_2O_4 \times HCl$ Calculated | C 50.57 | H 4.98 | N 5.13 |
| (546.30) Found | C 49.96 | H 5.49 | N 4.74 |

Example 4

(+)-N-[8(4-Chlorobenzyl)-6-hydroxy-3-nortropanyl]-2,6-dimethoxy-3-bromobenzamide-hydrochloride 10 g of the base (19.58 mmol) and 2.97 g of D (−) mandelic acid (19.58 mmol) are dissolved in about 15 ml of ethanol. Then sufficient ether is added (approx. 45 ml) to produce slight turbidity. Overnight at 20° C. the first crystals are formed; after the mixture has been left to stand for a further 72 hours crystallization is complete. The clear supernatant solution is decanted off. The crystals are washed twice with an ether/ethanol mixture (4:1), suction filtered and dried. 6.5 g of white crystals of the mandelate are obtained. The crude mandelate is further purified by first converting it into the base using 10% ammonia, extracting this base with ethyl acetate, drying it (sodium sulphate) and evaporating it down in vacuo. 4.7 g of white crystals are obtained. Fresh salt formation with D (−) mandelic acid and subsequent recycling into the base yield 2.06 g of the pure (+)-enantiomer with the specific rotation $[\alpha]^{25}$ of +11.8° (c=0.01; methanol).

Using methanolic hydrochloric acid, 2.1 g of white crystals of the (+)-hydrochloride are formed, m.p. 162°–175° C.

What is claimed is:

1. A compound of formula

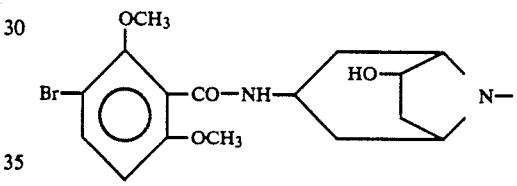

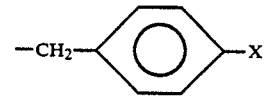

wherein X is fluoro or chloro or a physiologically acceptable acid addition salt thereof.

2. N-[8-(4-Fluorobenzyl)-6-hydroxy-3-nortropanyl]-2,6-dimethoxy-3-bromobenzamide or a physiologically acceptable acid addition salt thereof.

3. N-[8-(4-Chlorobenzyl)-6-hydroxy-3-nortropanyl]-2,6-dimethoxy-3-bromobenzamide or a physiologically acceptable acid addition salt thereof.

4. A pharmaceutical composition for suppressing CNS activity in a warm-blooded animal comprising a compound as recited in claim 1 and a pharmaceutically acceptable carrier.

5. A method for suppressing CNS activity in warm-blooded animals which comprises administering to said animals a therapeutically effective amount of compound as recited in claim 1.

* * * * *